United States Patent
Kornuta et al.

(10) Patent No.: US 11,475,304 B2
(45) Date of Patent: Oct. 18, 2022

(54) VARIATIONAL GRADIENT FLOW

(71) Applicant: INTERNATIONAL BUSINESS MACHINES CORPORATION, Armonk, NY (US)

(72) Inventors: Tomasz Kornuta, Los Gatos, CA (US); Ahmet Serkan Ozcan, Los Altos, CA (US); Deepta Rajan, San Jose, CA (US); Alexis Asseman, San Jose, CA (US); Chaitanya Shivade, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 336 days.

(21) Appl. No.: 16/872,907

(22) Filed: May 12, 2020

(65) Prior Publication Data
US 2021/0357743 A1 Nov. 18, 2021

(51) Int. Cl.
*G06N 3/08* (2006.01)
*G06N 3/04* (2006.01)
(Continued)

(52) U.S. Cl.
CPC ............. *G06N 3/08* (2013.01); *G06N 3/0454* (2013.01); *G16H 30/40* (2018.01); *G16H 50/20* (2018.01)

(58) Field of Classification Search
CPC ........ G06N 3/08; G06N 3/0454; G16H 50/20; G16H 30/40
See application file for complete search history.

(56) References Cited

U.S. PATENT DOCUMENTS 7,062,085 B2 * 6/2006 Luo .......................... G06T 7/11
382/165
9,152,926 B2 10/2015 Liang et al.
(Continued)

FOREIGN PATENT DOCUMENTS

WO WO-2019240900 A1 * 12/2019
WO WO-2021158409 A1 * 8/2021 ............... G06N 3/04

OTHER PUBLICATIONS

Chen et al., "GradNorm: Gradient Normalization for Adaptive Loss Balancing in Deep Multitask Networks," ICML: 793-802 (2018).
(Continued)

*Primary Examiner* — Shefali D Goradia
(74) *Attorney, Agent, or Firm* — Erik A. Huestis; Stephen J. Kenny; Foley Hoag, LLP

(57) ABSTRACT

According to embodiments of the present disclosure, methods of and computer program products for operating a plurality of classifiers are provided. A plurality of input entities are read, each input entity having an associated target label. The input entities are provided to a first classifier, and a category of each input entity is obtained therefrom. A feature map is determined for each input entity. Each feature map is provided to each of a set of classifiers, and an assigned label is obtained for each feature map from each of the set of classifiers. Each classifier is associated with one of the categories. For each classifier, the assigned label for each feature map is compared to the target labels to determine a plurality of gradients. The plurality of gradients are masked according to each category, yielding a masked set of gradients for each category. Each classifier is trained according its associated masked gradients.

19 Claims, 12 Drawing Sheets

(51) Int. Cl.
*G16H 30/40* (2018.01)
*G16H 50/20* (2018.01)

(56) References Cited

U.S. PATENT DOCUMENTS

| | | | |
|---|---|---|---|
| 9,269,156 B2* | 2/2016 | Birkbeck | G06T 7/11 |
| 9,792,492 B2 | 10/2017 | Soldevila et al. | |
| 10,074,041 B2* | 9/2018 | Zhou | G06V 10/82 |
| 10,339,466 B1 | 7/2019 | Ding et al. | |
| 10,354,122 B1* | 7/2019 | He | G06T 7/97 |
| 10,423,861 B2 | 9/2019 | Gao et al. | |
| 2005/0266395 A1* | 12/2005 | Gholap | G06T 7/0012 |
| | | | 702/19 |
| 2007/0118492 A1 | 5/2007 | Bahlmann et al. | |
| 2017/0228645 A1 | 8/2017 | Wang et al. | |
| 2018/0253645 A1* | 9/2018 | Burr | G06N 3/08 |
| 2018/0342090 A1 | 11/2018 | Ganguli | |
| 2018/0373963 A1 | 12/2018 | Lo et al. | |
| 2019/0095818 A1 | 3/2019 | Varadarajan et al. | |
| 2019/0130275 A1 | 5/2019 | Chen et al. | |
| 2019/0220758 A1 | 7/2019 | Talyansky et al. | |
| 2019/0244139 A1 | 8/2019 | Varadarajan et al. | |
| 2020/0082167 A1* | 3/2020 | Shalom | G06V 20/52 |
| 2020/0226459 A1* | 7/2020 | Chen | G06N 3/0454 |
| 2020/0302246 A1* | 9/2020 | Shen | G06N 3/0454 |
| 2021/0125061 A1* | 4/2021 | Munoz Delgado | |
| | | | G06F 16/90335 |
| 2021/0214765 A1* | 7/2021 | Deshpande | G06V 10/82 |

OTHER PUBLICATIONS

Galarraga., "Interpretability In Classifiers," Inventeurs Du Monde Numerique: 1-70 (2019).

Gao et al., "Deep Generative Learning via Variational Gradient Flow," ICML: 1-9 (2019).

Sinha et al., "Gradient Adversarial Training of Neural Networks," Machine Learning: 1-13 (2018).

Zhu et al., "B-CNN: Branch Convolutional Neural Network for Hierarchical Classification," Computer Vision and Pattern Recognition: 1-9 (2017).

* cited by examiner

VARIATIONAL GRADIENT FLOW

BACKGROUND

Embodiments of the present disclosure relate to training and operation of classifiers, and more specifically, to variational gradient flow in multiple classifier models.

BRIEF SUMMARY

According to embodiments of the present disclosure, methods of and computer program products for operating a plurality of classifiers are provided. In various embodiments, a method is provided where a plurality of input entities are read. Each of the input entities has an associated target label. In various embodiments, the input entities are provided to a first classifier, and a category of each of the input entities is obtained therefrom. In various embodiments, a feature map is determined for each of the input entities. In various embodiments, each of the feature maps is provided to each of a set of classifiers, and from each of the set of classifiers an assigned label is obtained for each of the plurality of feature maps. Each of the set of classifiers is associated with one of the categories. In various embodiments, for each of the set of classifiers, the assigned label for each of the plurality of feature maps is compared to the target labels, to determine a plurality of gradients. In various embodiments, the plurality of gradients are masked according to each category, yielding a masked set of gradients for each of the categories. In various embodiments, each of the set of classifiers is trained according its associated masked gradients.

In various embodiments, an input entity is provided to the first classifier, and a category of the input entity in obtained therefrom, a feature map for the input entity is determined, the feature map is provided to each of a set of classifiers, and a label for the feature map is obtained from each of the set of classifiers, the labels are masked according to the category, and the masked labels are outputted. In various embodiments, each of the plurality of input entities includes an image. In various embodiments, the first classifier is pre-trained. In various embodiments, the first classifier comprises an artificial neural network. In various embodiments, each of the set of classifiers comprises an artificial neural network. In various embodiments, each of the target labels is a member of one of the categories.

In various embodiments, a system of the present disclosure includes a computing node comprising a computer readable storage medium having program instructions embodied therewith. The program instructions are executable by a processor of the computing node to cause the processor to perform a method where a plurality of input entities are read. Each of the input entities has an associated target label. In various embodiments, the input entities are provided to a first classifier, and a category of each of the input entities is obtained therefrom. In various embodiments, a feature map is determined for each of the input entities. In various embodiments, each of the feature maps is provided to each of a set of classifiers, and from each of the set of classifiers an assigned label is obtained for each of the plurality of feature maps. Each of the set of classifiers are associated with one of the categories. In various embodiments, for each of the set of classifiers, the label for each of the plurality of feature maps is compared to the target labels, to determine a plurality of gradients. In various embodiments, the plurality of gradients are masked according to each category, yielding a masked set of gradients for each of the categories. In various embodiments, each of the set of classifiers is trained according its associated masked gradients.

In various embodiments, an input entity is provided to the first classifier, and a category of the input entity in obtained therefrom, a feature map for the input entity is determined, the feature map is provided to each of a set of classifiers, and a label for the feature map is obtained from each of the set of classifiers, the labels are masked according to the category, and the marks labels are outputted. In various embodiments, each of the plurality of input entities includes an image. In various embodiments, the first classifier is pre-trained. In various embodiments, the first classifier comprises an artificial neural network. In various embodiments, each of the set of classifiers comprises an artificial neural network. In various embodiments, each of the target labels is a member of one of the categories.

In various embodiments, a computer program product for operating a plurality of classifiers is provided including a computer readable storage medium having program instructions embodied therewith. The program instructions are executable by a processor of the computing node to cause the processor to perform a method where a plurality of input entities are read. Each of the input entities has an associated target label. In various embodiments, the plurality of input entities are provided to a first classifier, and a category of each of the input entities are obtained therefrom. In various embodiments, a feature map is determined for each of the plurality of input entities. In various embodiments, each of the feature maps are provided to each of a set of classifiers, and from each of the set of classifiers a label is obtained for each of the plurality of feature maps. Each of the set of classifiers is associated with one of the categories. In various embodiments, for each of the set of classifiers, the label for each of the plurality of feature maps is compared to the target labels, to determine a plurality of gradients. In various embodiments, the plurality of gradients are masked according to each category, yielding a masked set of gradients for each of the categories. In various embodiments, each of the set of classifiers is trained according its associated masked gradients.

In various embodiments, an input entity is provided to the first classifier, and a category of the input entity in obtained therefrom, a feature map for the input entity is determined, the feature map is provided to each of a set of classifiers, and a label for the feature map is obtained from each of the set of classifiers, the labels are masked according to the category, and the marks labels are outputted. In various embodiments, each of the plurality of input entities includes an image. In various embodiments, the first classifier is pre-trained. In various embodiments, the first classifier comprises an artificial neural network. In various embodiments, each of the set of classifiers comprises an artificial neural network. In various embodiments, each of the target labels is a member of one of the categories.

According to embodiments of the present disclosure, methods of and computer program products for operating a plurality of classifiers are provided. In various embodiments, a method is provided where data are inputted into both: i) a plurality of fine-grained classifiers, and ii) a course-grained classifier. The coarse grained classifier is configured to categorize the input data among a plurality of masking modules. Each of the plurality of masking modules corresponds to one of the plurality of fine-grained classifiers. During a training phase, a loss function is computed corresponding to each pair of the fine-grained classifiers and masking modules. During an inference phase, the data are assigned to a particular class in view of output from the plurality of fine-grained classifiers and the plurality of masking modules.

In various embodiments, the data comprise a plurality of images. In various embodiments, the coarse classifier is pre-trained. In various embodiments, the coarse classifier comprises an artificial neural network. In various embodiments, each of the plurality of fine-grained classifiers comprises an artificial neural network.

DETAILED DESCRIPTION

Artificial neural networks (ANNs) are distributed computing systems, which consist of a number of neurons interconnected through connection points called synapses. Each synapse encodes the strength of the connection between the output of one neuron and the input of another. The output of each neuron is determined by the aggregate input received from other neurons that are connected to it. Thus, the output of a given neuron is based on the outputs of connected neurons from preceding layers and the strength of the connections as determined by the synaptic weights. An ANN is trained to solve a specific problem (e.g., pattern recognition) by adjusting the weights of the synapses such that a particular class of inputs produce a desired output.

Various algorithms may be used for this learning process. Certain algorithms may be suitable for specific tasks such as image recognition, speech recognition, or language processing. Training algorithms lead to a pattern of synaptic weights that, during the learning process, converges toward an optimal solution of the given problem. Backpropagation is one suitable algorithm for supervised learning, in which a known correct output is available during the learning process. The goal of such learning is to obtain a system that generalizes to data that were not available during training.

In general, during backpropagation, the output of the network is compared to the known correct output. An n error value is calculated for each of the neurons in the output layer. The error values are propagated backwards, starting from the output layer, to determine an error value associated with each neuron. The error values correspond to each neuron's contribution to the network output. The error values are then used to update the weights. By incremental correction in this way, the network output is adjusted to conform to the training data.

When applying backpropagation, an ANN rapidly attains high accuracy on most of the examples in a training-set. The vast majority of training time is spent trying to further increase this test accuracy. During this time, a large number of the training data examples lead to little correction, since the system has already learned to recognize those examples. While in general, ANN performance tends to improve with the size of the data set, this can be explained by the fact that larger data-sets contain more borderline examples between the different classes on which the ANN is being trained.

Figure 1:
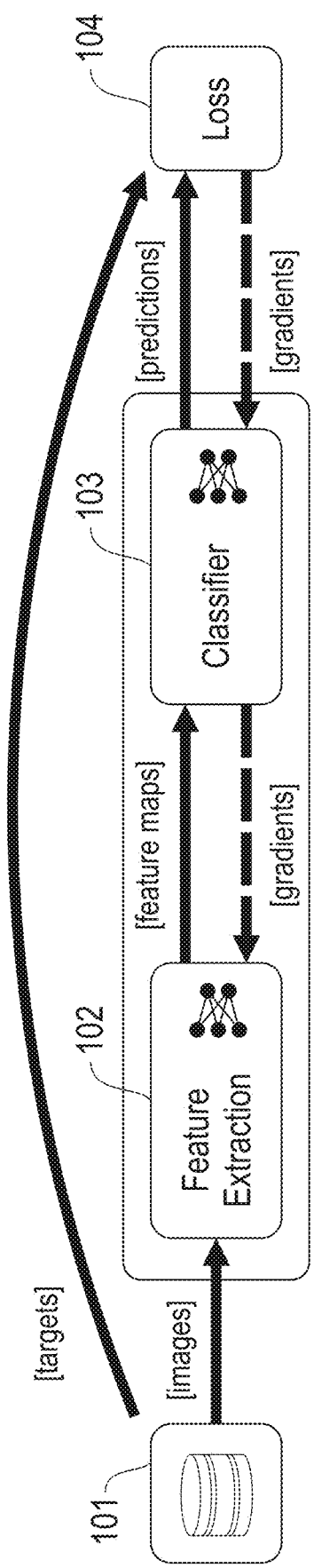
FIG. 1 illustrates an exemplary data flow for single input, single output machine learning model training.

Referring to FIG. 1, an exemplary data flow is illustrated for single input, single output machine learning model training. In this example, an image classification dataset 101, such as MNIST or CIFAR10, provides input images and target labels. In other examples, the inputs may be other data for classification. Input images are provided to a feature extraction stage 102. In some embodiments, the feature extraction stage comprises an artificial neural network, or one of more layers thereof. A feature map for each input is provided to the classifier stage 103. In some embodiments, the classifier stage comprises an artificial neural network, or one of more layers thereof. Output predictions are provided to loss stage 104, which compares them against the target values (e.g., ground truth image labels). Based on this comparison, gradients are propagated back through classifier stage 103 and/or feature extraction stage 102 in order to update neural network weights. It will be appreciated that while various examples provided herein refer to input images, the present disclosure is applicable to a variety of input entities, including text, images, video, and arbitrary feature vectors.

The example in FIG. 1 is suitable for single input, single output tasks. However, it will be appreciated that many classification tasks involve auxiliary information. For example, more complex machine learning tasks may involve multiple tiers of classification, such as a Class and Superclass. An exemplary set of classes and superclasses is provided in Table 1. In this case, Superclass is a coarse group classification (e.g., aquatic mammals) and Class is a specific type within the Superclass (e.g., dolphin). Classification tasks of this type exist in vision and language domains, and may be referred to as "tasks with auxiliary information." Example datasets include CIFAR-100 and WordNet.

TABLE 1

| Superclass | Classes |
|---|---|
| aquatic mammals | beaver, dolphin, otter, seal, whale |
| fish | aquarium fish, flatfish, ray, shark, trout |
| flowers | orchids, poppies, roses, sunflowers, tulips |

Another example of a complex task is multimodal classification. In an exemplary multimodal task in the medical imaging domain, multiple inputs result in a single output. In one example, the medical visual question answering (Med VQA) dataset contains an image and a question as an input. The single output is an answer. Exemplary questions are grouped into four categories: determine the modality of the image; determine the plane of the image; identify the organ/anatomy of interest in the image; and identify the abnormality in the image.

It will be appreciated that a variety of additional datasets of interest include rich or auxiliary information. Examples include: CLEVR—a visual question answering dataset which comes with images, questions, scene descriptions; GQA—a visual question answering dataset which comes with images, questions, scene descriptions, relational graphs; and MS COCO—a vision dataset for image classification, object detection, segmentation, pose estimation.

Figure 2:
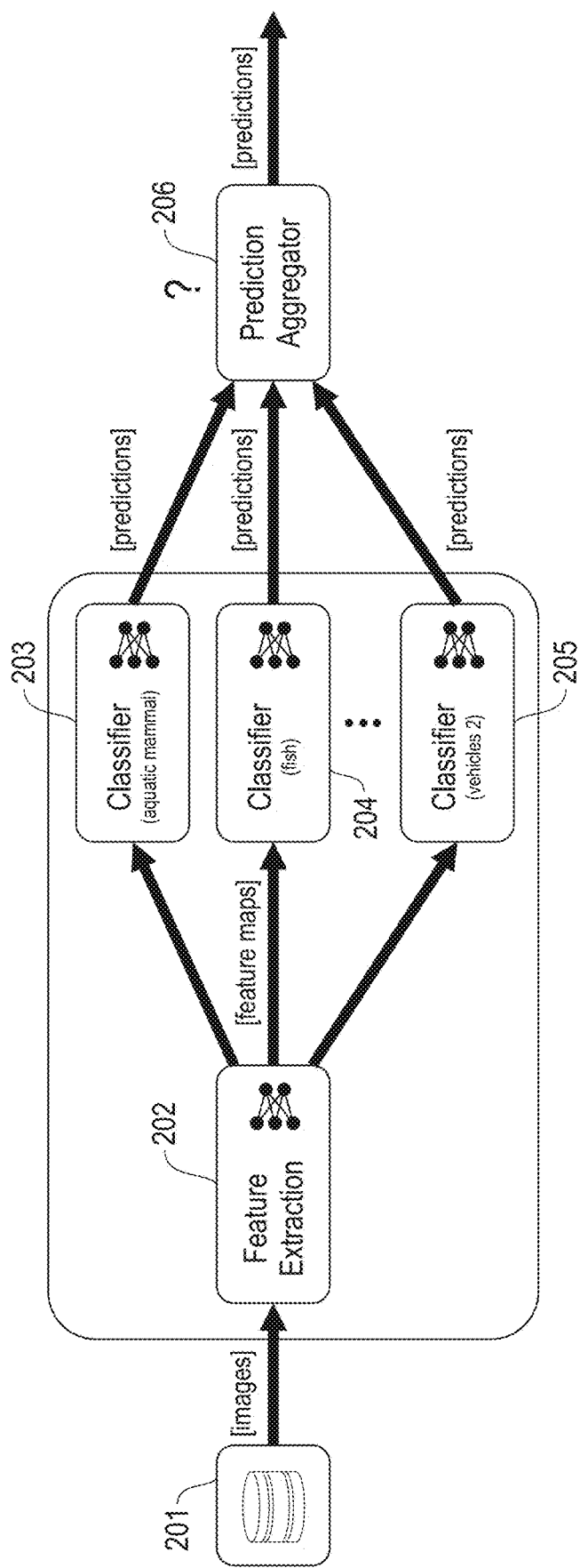
FIG. 2 illustrates an exemplary model architecture using specialized classifiers according to embodiments of the present disclosure.

Referring now to FIG. 2, an exemplary architecture using specialized classifiers is illustrated. In this example, multiple classifiers and a prediction aggregator are provided, thereby incorporating domain knowledge into the overall model.

In this example, an image classification dataset 201, such as CIFAR-100, provides input images and target labels. In other examples, the inputs may be other data for classification. Input images are provided to a feature extraction stage 202. In some embodiments, the feature extraction stage comprises an artificial neural network, or one of more layers thereof. A feature map for each input is provided to each of a plurality of classifier stages 203 . . . 205. In some embodiments, each classifier stage comprises an artificial neural network, or one of more layers thereof. Output predictions are provided to an aggregator 206, which determines an overall prediction. The overall prediction may be compared against the target values (e.g., ground truth image labels) in a training phase.

In this way, domain knowledge is incorporated into the overall model. Further details of this approach are described below.

Figure 3A:
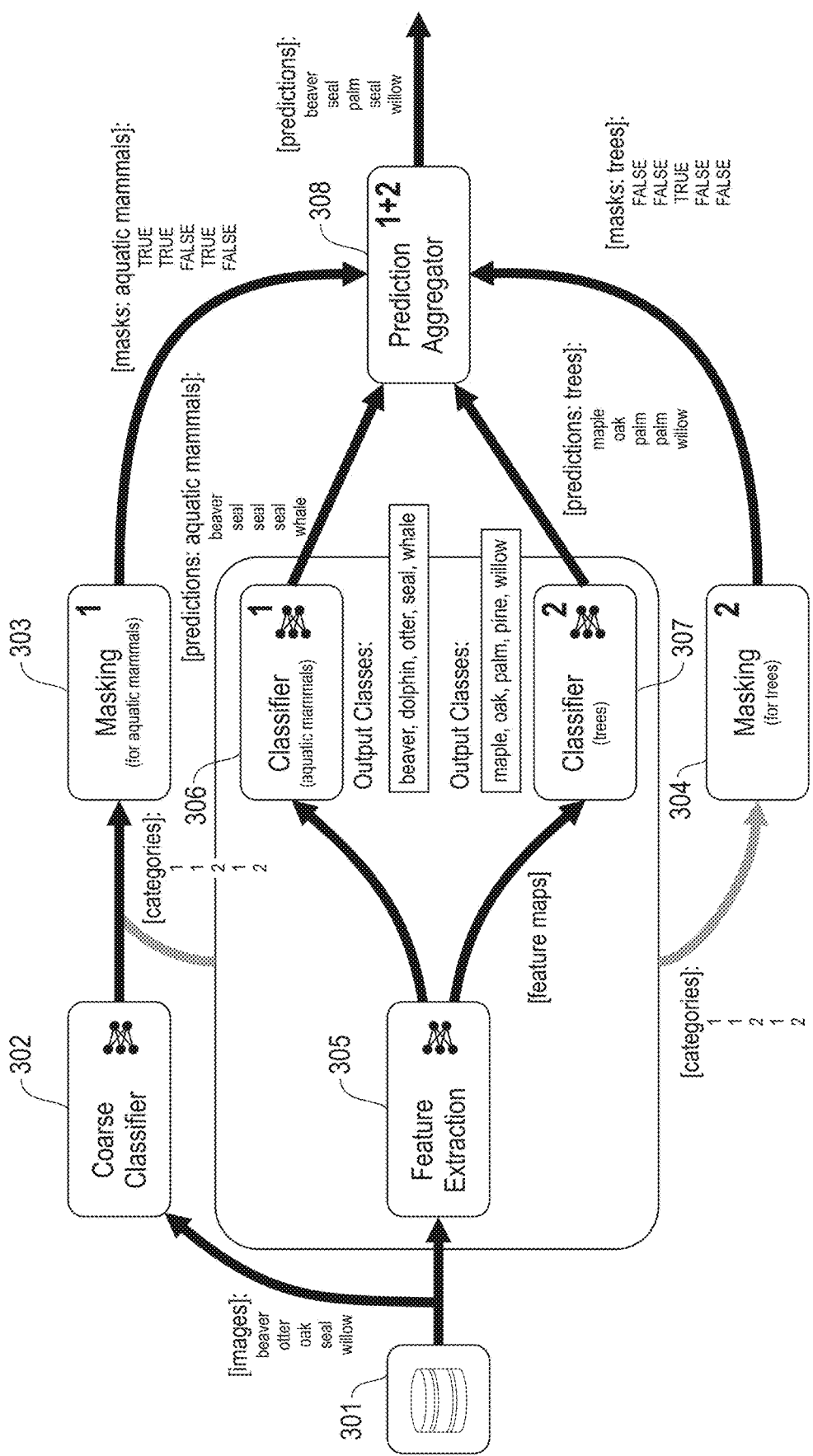
FIGS. 3A-C illustrate a domain-specific model using specialized classifiers according to embodiments of the present disclosure.
Figure 3B:
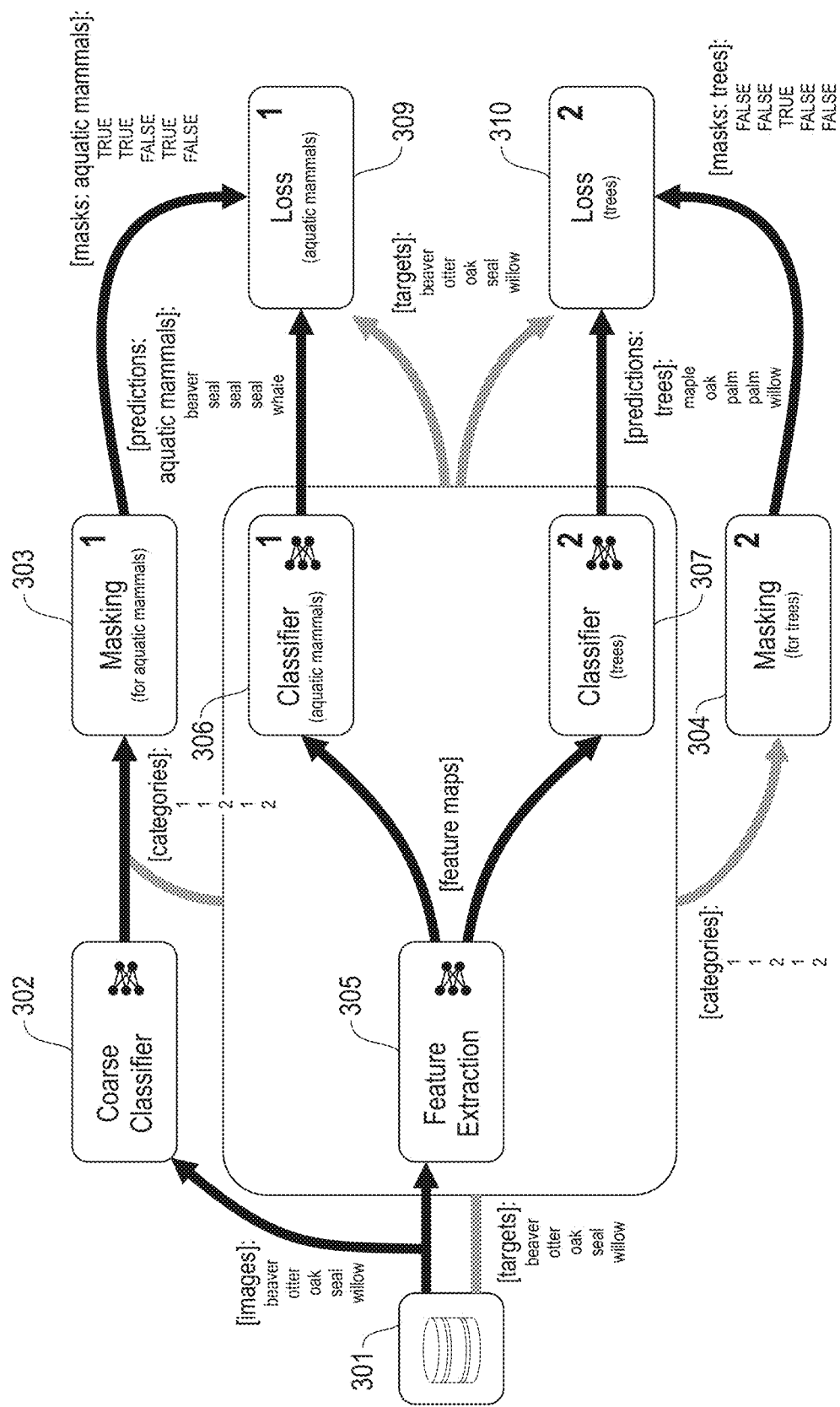
Figure 3C:
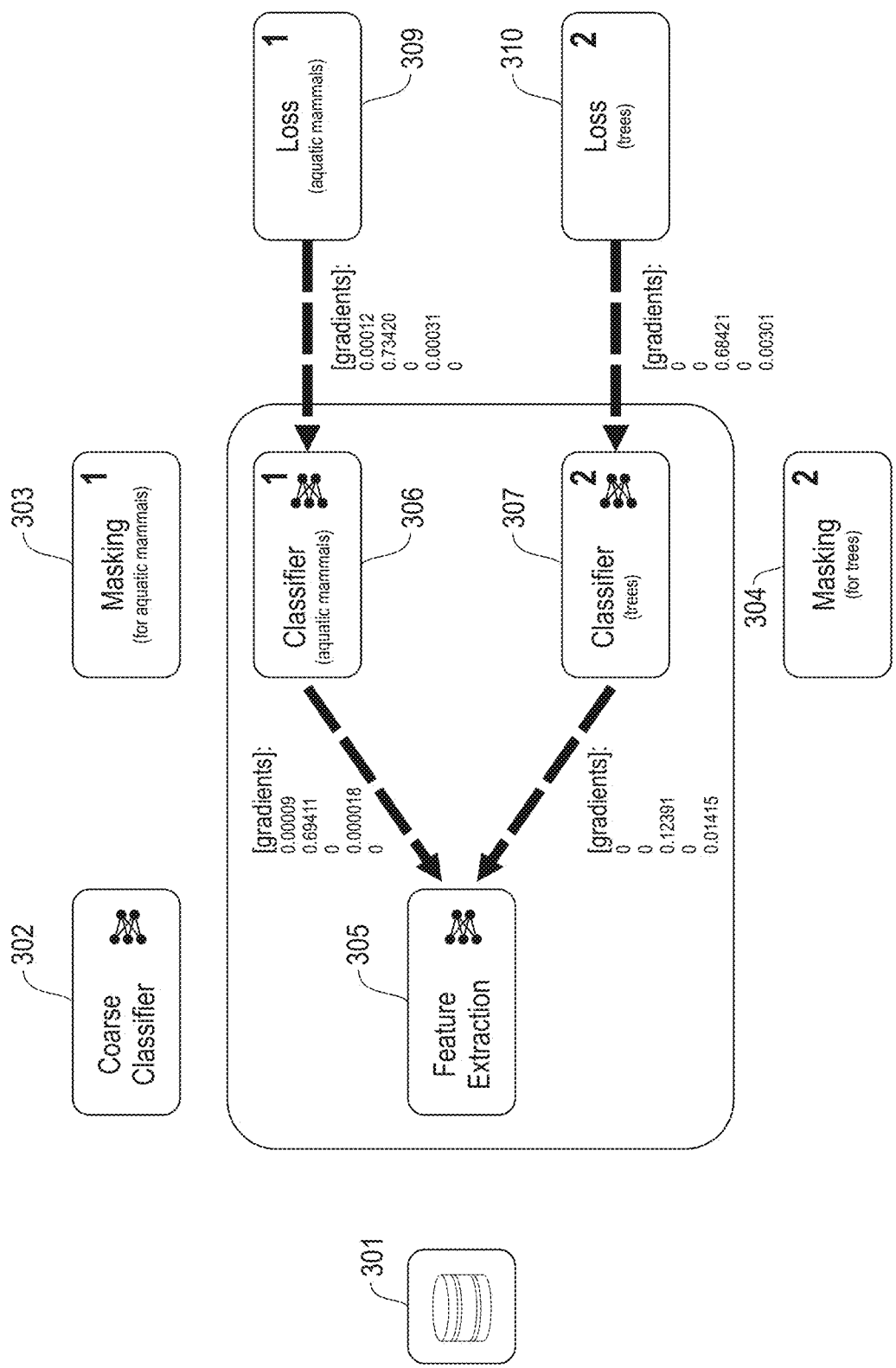

Referring to FIG. 3A-3C, a domain-specific model according to embodiments of the present disclosure is illustrated.

In this example, an image classification dataset 301, such as CIFAR-100, provides input images and target labels. In other examples, the inputs may be other data for classification. Input images are provided to a coarse classifier 302. In some embodiments, the coarse classifier comprises an artificial neural network, or one of more layers thereof. In some embodiments, the coarse classifier is either pretrained and frozen or is hardcoded. Coarse classifier 302 provides masking 303 . . . 304 for each of a set of superclasses (e.g., aquatic mammals, trees). Input images are also provided to a feature extraction stage 305. In some embodiments, the feature extraction stage comprises an artificial neural network, or one of more layers thereof. A feature map for each input is provided to each of a plurality of classifier stages 306 . . . 307. In some embodiments, each classifier stage comprises an artificial neural network, or one of more layers thereof. Output predictions are provided to an aggregator 308 along with masking 303 . . . 304. Aggregator 308 determines an overall prediction.

In FIG. 3A, a forward (inference) pass is illustrated. In this example, five images are provided to the coarse classifier 302 and feature extraction 305 stages. The course classifier assigns categories, in this case either 1: aquatic mammals or 2: trees. Each classifier provides an inferred output class for each input image irrespective of the output of the coarse classifier. Masks are generated for each category—in this case, as there are two classes, the masking vectors have opposite value for corresponding entries. The prediction aggregator then applies the masking vectors to the output of each corresponding classifier in order to arrive at an aggregated prediction. The aggregated prediction includes the prediction from the classifier selected based on the category masking value.

In FIG. 3B, a forward pass during training is illustrated. Training is composed of forward and backward passes. The masking is needed during training because the system needs to learn which classifiers to mask. In this example, five images are provided to the coarse classifier 302 and feature extraction 305 stages. The target labels are provided to loss stages 309 . . . 310, which compares them against the target values (e.g., ground truth image labels).

In FIG. 3C, a backward pass during training is illustrated. Based on the comparison performed in loss stages 309 . . . 310, gradients are propagated back through classifier stages 306 . . . 307 and/or feature extraction stage 305 in order to update neural network weights. The mask vectors are applied during the backpropagation phase to zero out categories, which prevents the flow of gradients to classifiers not applicable to a given category. As a result, irrelevant samples do not affect the weights and negatively influence the accuracy of the classifiers. The specialized classifiers are thus trained only with relevant samples.

As set out above, systems according to various embodiments comprise a feature extractor, a coarse classifier, a plurality of specialized classifiers, a plurality of masking modules, a plurality of loss modules, and a prediction aggregator.

In various embodiments, the feature extractor is a deep convolutional neural network. In some embodiments, the feature extractor is pre-trained on a different dataset (e.g., ImageNet) and then fine-tuned (e.g., top layers of the network continue to be trained) during training.

In various embodiments, the coarse classifier is a pre-trained neural network with frozen weights. In such embodiments, the synaptic weights of this neural network will not change during the training of the whole system. This classifier classifies the inputs in coarse categories. In particular, a plurality of inputs (e.g., a batch of images) is mapped to a plurality of outputs (e.g., categories).

In various embodiments, the multiple specialized classifiers are neural networks that act as specialized classifiers. The weights of these neural networks will be adjusted during the whole system training.

In various embodiments, the multiple masking modules produce masks (e.g., a set of TRUE and FALSE flags), so that during the training, gradient flow will be controlled.

In various embodiments, the multiple loss modules compute a loss function for the plurality of classifiers.

In various embodiments, a prediction aggregator is responsible for the aggregation of the predictions (i.e. outputs of the specialized neural networks).

In various embodiments, one or more input encoders is shared by some or all of the specialized classifiers. In this case, the system contains multiple input encoders.

Figure 4:
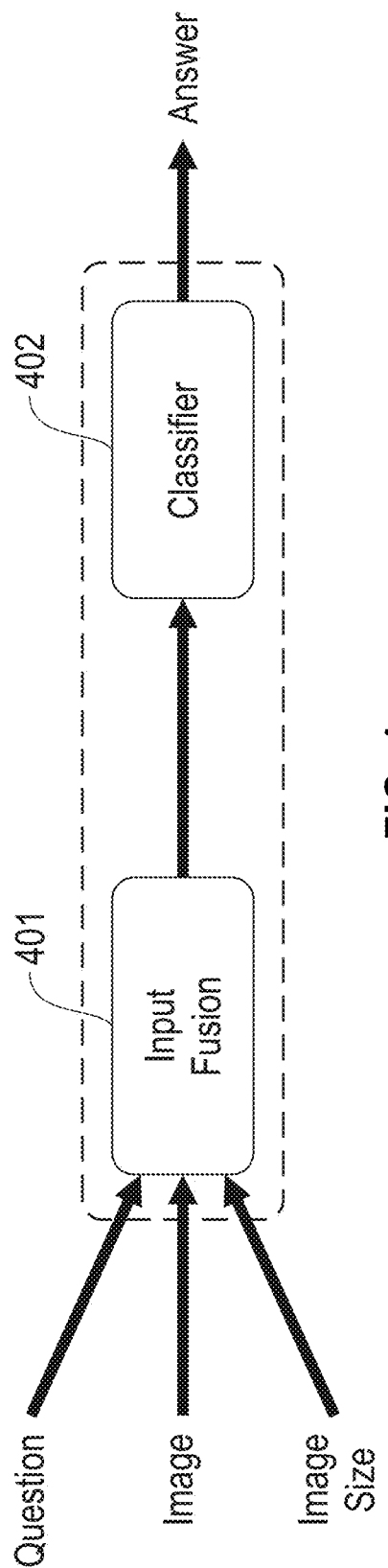
FIG. 4 is a schematic view of an exemplary single classifier model.
Figure 5:
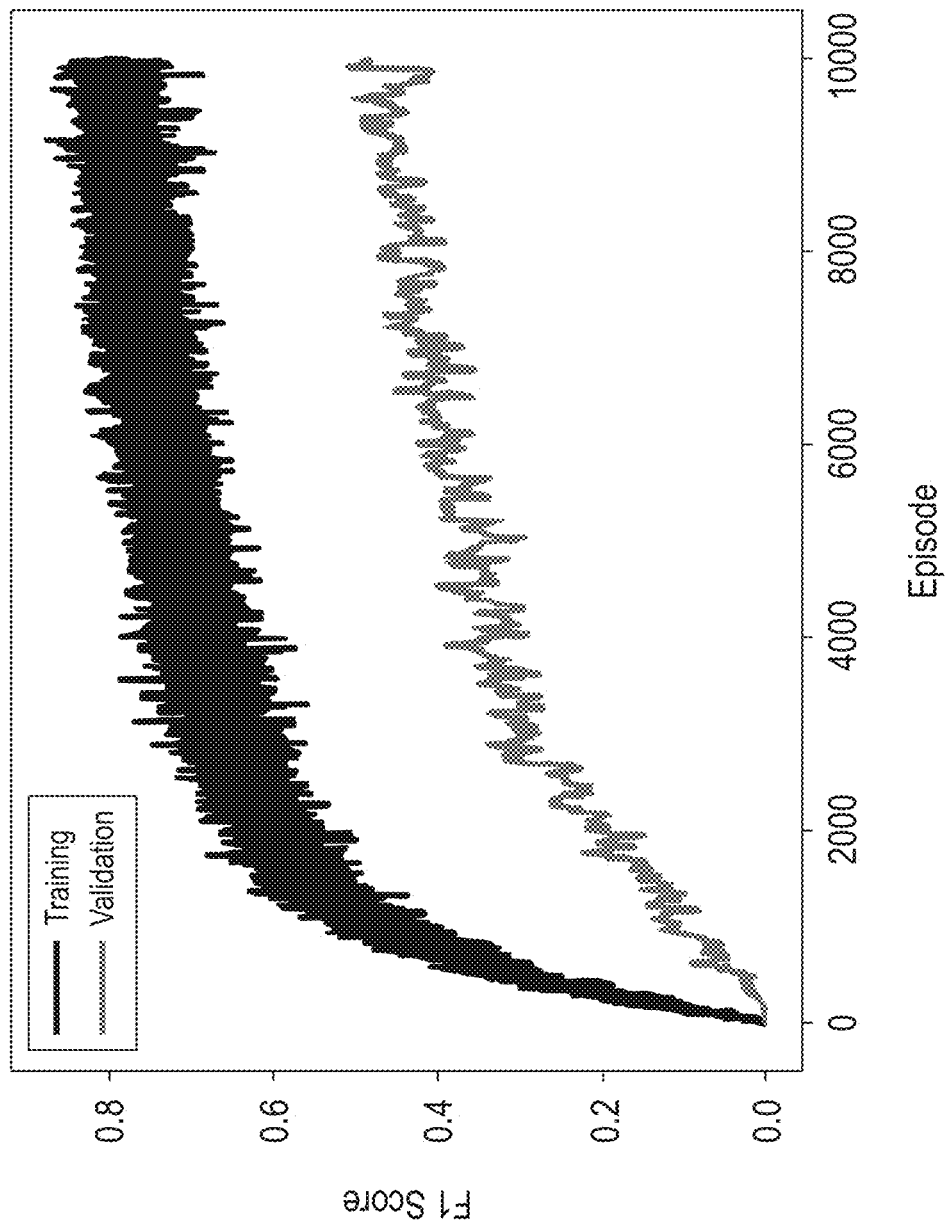
FIG. 5 is a plot of F1 scores for an exemplary single classifier case.

Referring now to FIG. 4-5, exemplary results are provided using one classifier. In this example, the Med-VQA 2019 dataset is considered for the medical visual question answering problem. In this example, there is only one classifier. FIG. 4 provides a schematic view of the model employed. In this example, an input question, an image, and an image size are provided as inputs to input fusion stage 401. The combined input features are provided to a single classifier 402.

Table 2 shows the average precision, recall and F-1 score metrics for the single classifier case. The question answering dataset is setup as a classification task, with answers corresponding to pre-defined classes rather than being generated. In this case, there is one classifier that learns to answer all 4 sub tasks.

TABLE 2

|  | Precision | Recall | F-1 Score |
|---|---|---|---|
|  | 0.6002 | 0.4365 | 0.4776 |
|  | 0.5741 | 0.4311 | 0.4702 |
|  | 0.6349 | 0.4459 | 0.4881 |
|  | 0.6607 | 0.4392 | 0.4893 |
|  | 0.6777 | 0.4243 | 0.4813 |
| Average: | 0.62952 | 0.4354 | 0.4813 |

FIG. 5 plots the F1 score for the single classifier case.

Figure 6:
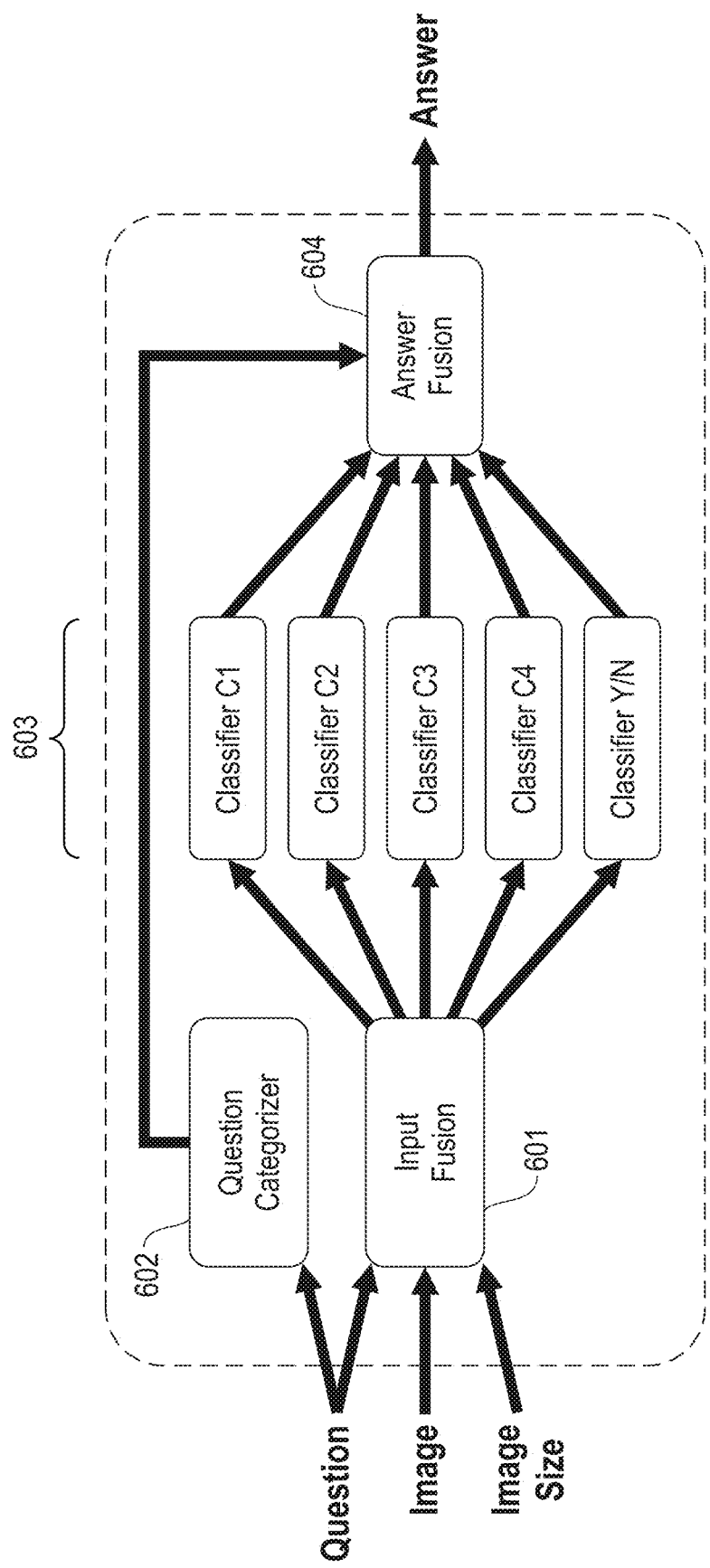
FIG. 6 is a schematic view of an exemplary multiple classifier model according to embodiments of the present disclosure.
Figure 7:
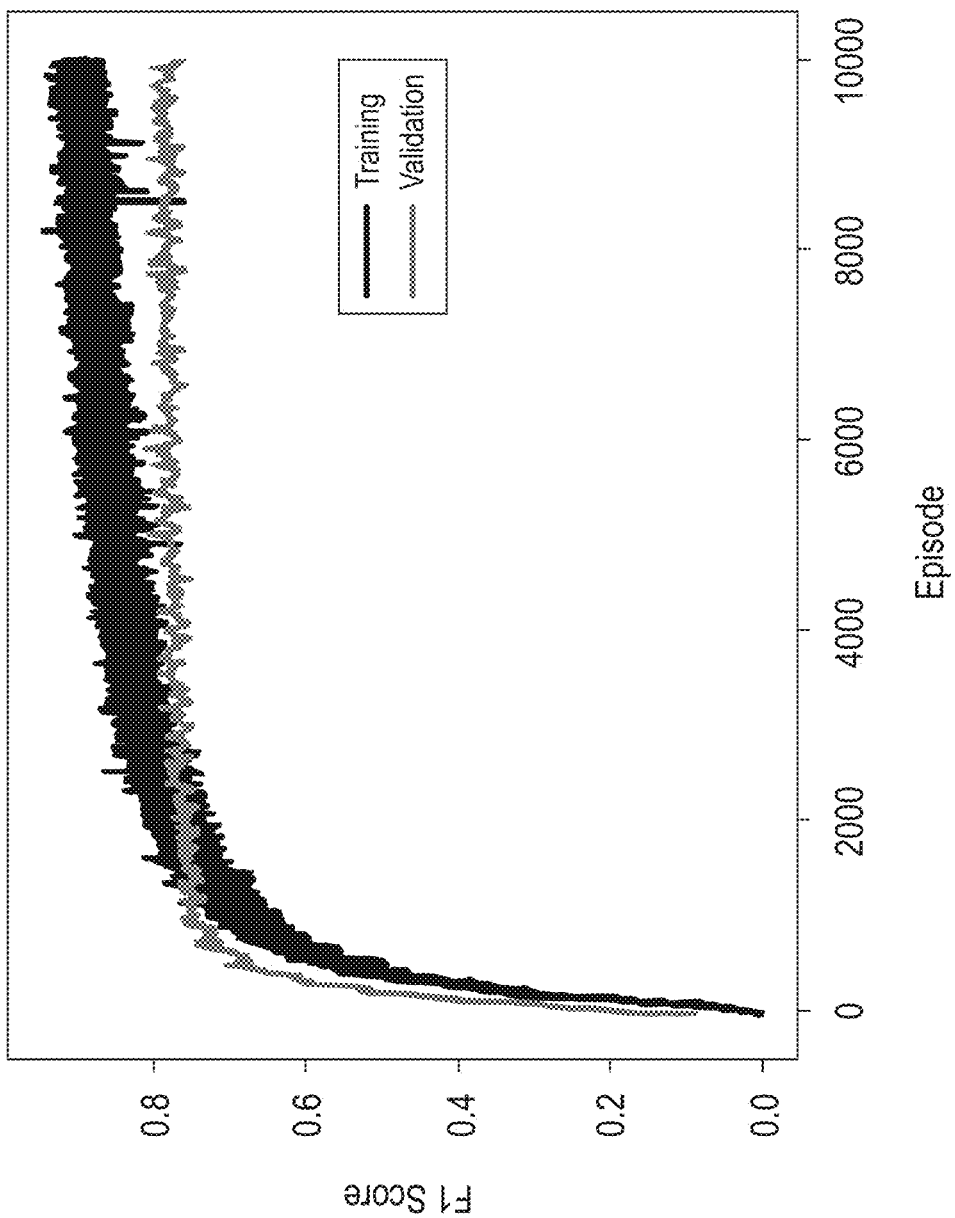
FIG. 7 is a plot of F1 scores for an exemplary multiple classifier case.

Referring now to FIG. 6-7, exemplary results are provided using five classifiers in the architecture described above. In this example, the Med-VQA 2019 dataset is considered for the medical visual question answering problem. FIG. 6 provides a schematic view of the model employed. The training procedure and all hyperparameters employed are the same for both the one classifier and five classifier examples. In this example, an input question, an image, and an image size are provided as inputs to input fusion stage 601. In addition, the question is provided to categorizer 602, which determines the question type (and thus corresponds to a coarse classifier as described above). The combined input features are provided to a plurality of classifiers 603. The results of the classifiers are combined according to the question category in answer fusion stage 604. This process corresponds to the prediction aggregator process described above.

Table 3 shows the average precision, recall and F-1 score metrics for the five-classifier case. The question answering dataset is setup as a classification task, with answers corresponding to pre-defined classes rather than being generated.

TABLE 3

|  | Precision | Recall | F-1 Score |
|---|---|---|---|
|  | 0.7328 | 0.7324 | 0.7325 |
|  | 0.7475 | 0.7459 | 0.7464 |
|  | 0.7832 | 0.7824 | 0.7825 |
|  | 0.7327 | 0.7351 | 0.7352 |
|  | 0.8049 | 0.8041 | 0.8043 |
| Average: | 0.76022 | 0.75998 | 0.76018 |

FIG. 7 plots the F1 score for the five-classifier case.

These results demonstrate the advantage of the multiple classifier architecture described herein.

To arrive at the above architecture, the dataset was analyzed to identify five sub-categories (four categories of questions and one binary yes/no category). Therefore, the question categorizer learns to choose the appropriate classifier and mask the flow of gradients back to the other classifiers. For example, if the question is a yes/no type, the categorizer masks the gradient flow back to C1, C2, C3 and C4. The neural network system learns this through training with input/output examples.

Figure 8:
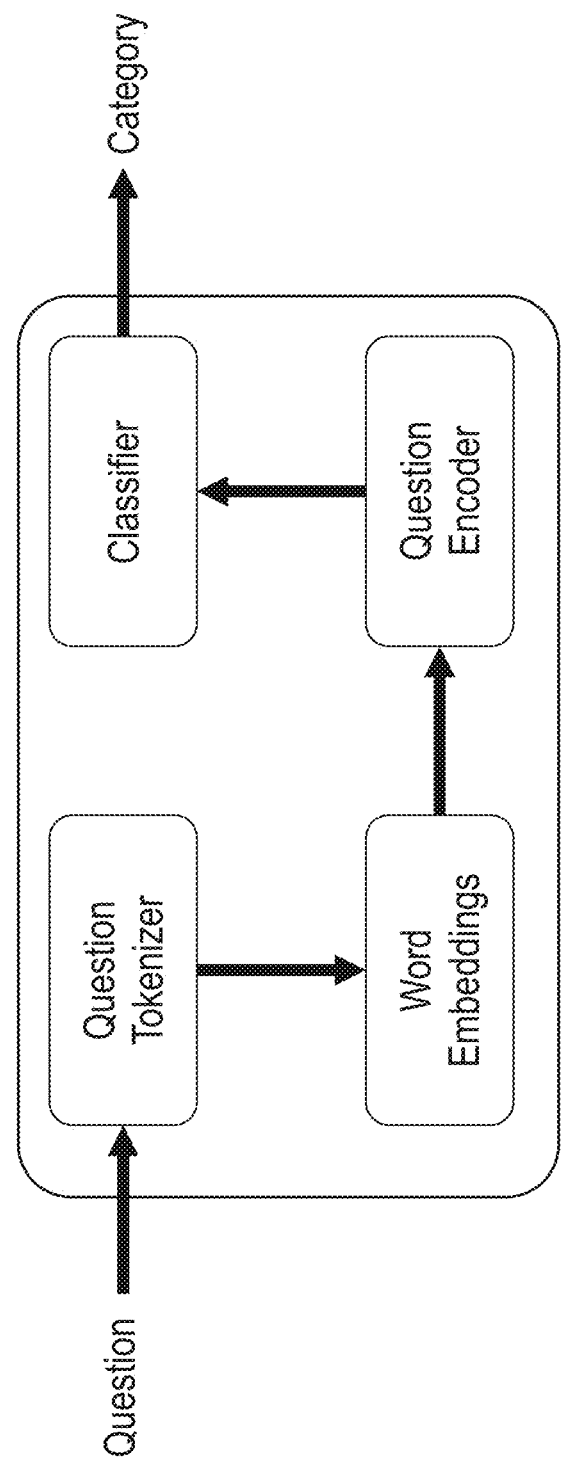
FIG. 8 illustrates an exemplary implementation of a coarse classifier according to embodiments of the present disclosure.

FIG. 8 illustrates an exemplary implementation of a question classifier, as used in the example of FIG. 6. In this example, a question is tokenized, word embeddings are determined, and the question is encoded before providing the resulting features to a classifier. The classifier outputs the category for use in the answer fusion stage. It will be appreciated that this is merely an example of a coarse classifier suitable for use in the architecture described above.

As shown above, the present disclosure provides architectures exhibiting improved accuracy and faster training and convergence. Specialized classifiers allow better interpretability through utilization of auxiliary domain knowledge.

Figure 9:
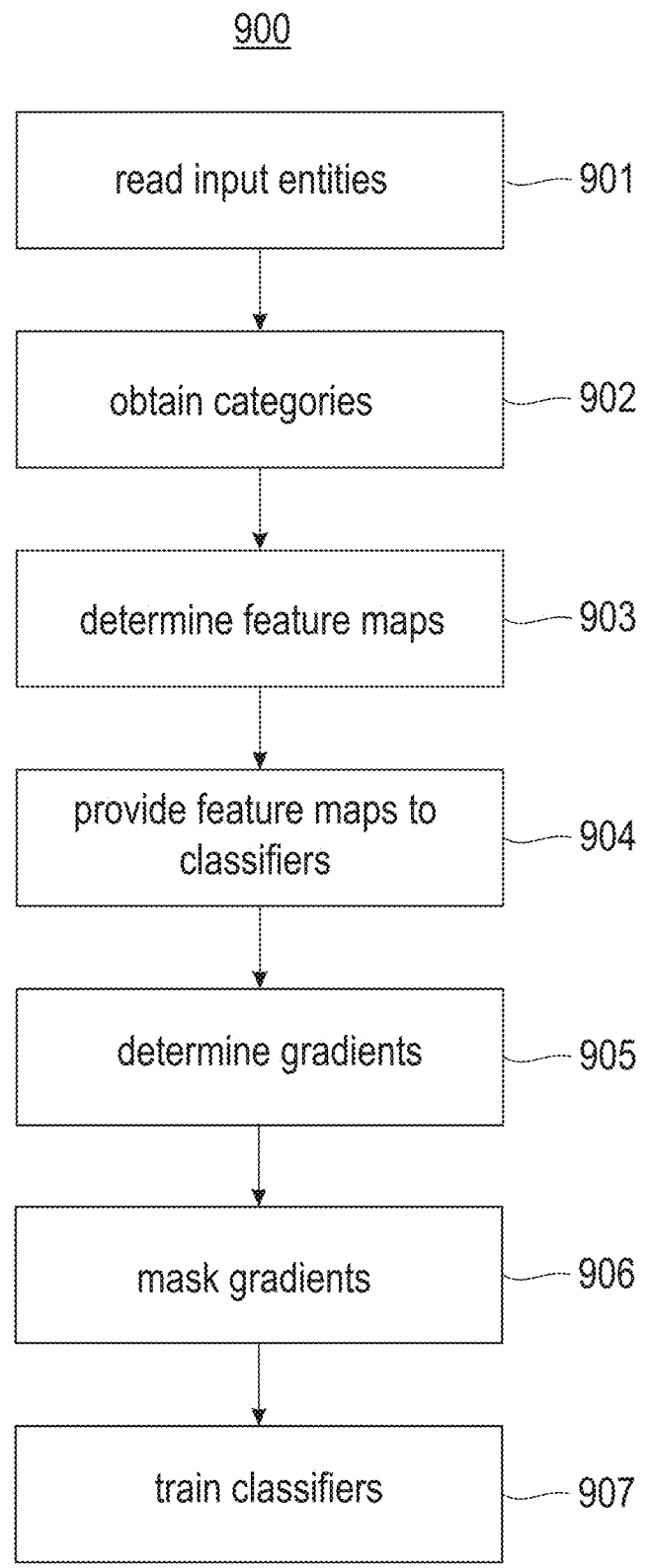
FIG. 9 illustrates a method of operating a plurality of classifiers according to embodiments of the present disclosure.

With reference now to FIG. 9, a method 900 of operating a plurality of classifiers is illustrated. At 901, a plurality of input entities are read. Each of the input entities have an associated target label. At 902, the plurality of input entities are provided to a first classifier, and a category of each of the input entities are obtained therefrom. At 903, a feature map is determined for each of the plurality of input entities. At 904, each of the feature maps are provided to each of a set of classifiers, and from each of the set of classifiers a label is obtained for each of the plurality of feature maps. Each of the set of classifiers are associated with one of the categories. At 905, for each of the set of classifiers, the label for each of the plurality of feature maps is compared to the target labels, to determine a plurality of gradients. At 906, the plurality of gradients are masked according to each category, yielding a masked set of gradients for each of the categories. At 907, each of the set of classifiers are trained according its associated masked gradients.

Figure 10:
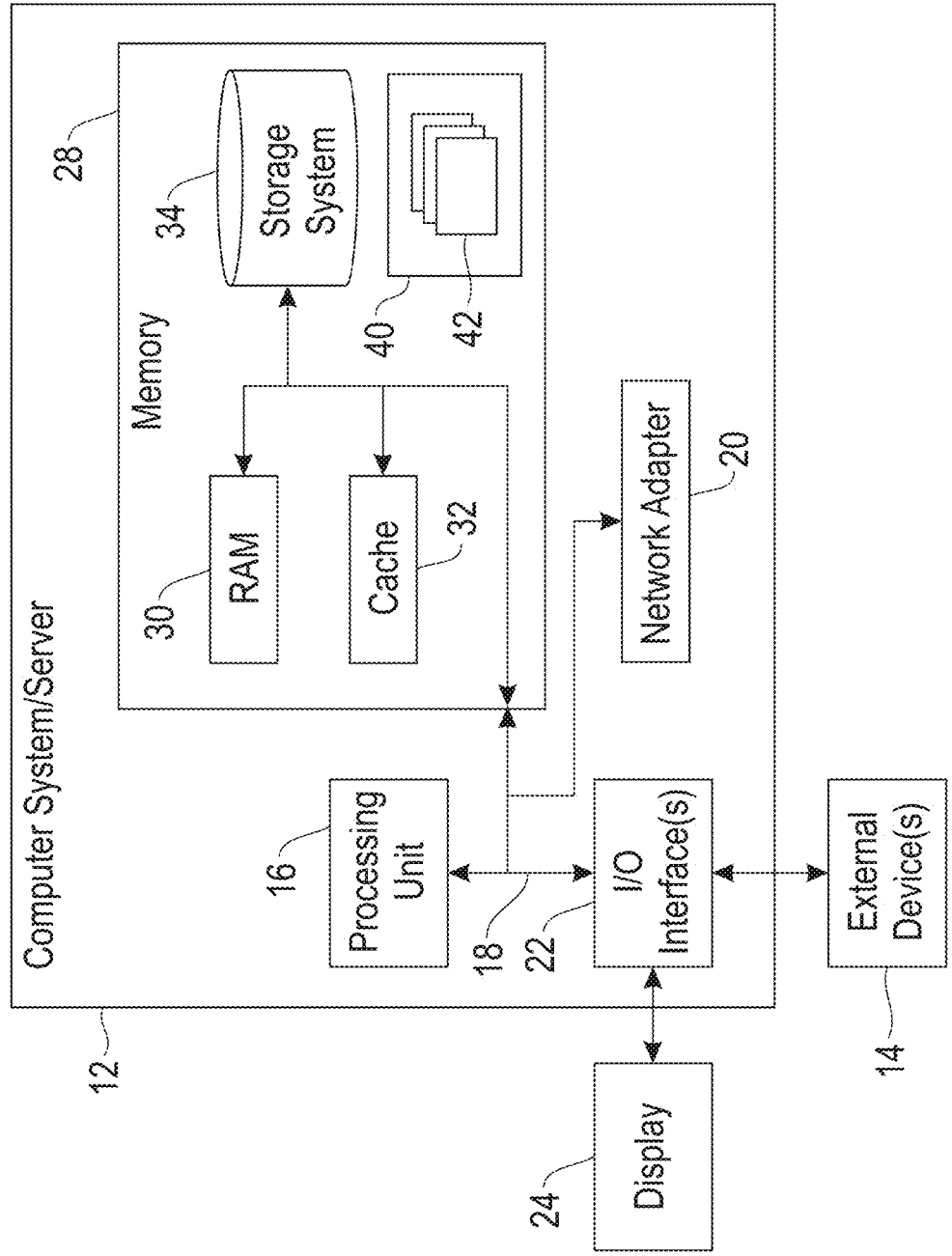
FIG. 10 depicts a computing node according to an embodiment of the present disclosure.

Referring now to FIG. 10, a schematic of an example of a computing node is shown. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 10, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCIe), and Advanced Microcontroller Bus Architecture (AMBA).

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present disclosure may be embodied as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   reading a plurality of input entities, each of the input entities having an associated target label;
   providing the input entities to a first classifier, and obtaining therefrom a category of each of the input entities;
   determining a feature map for each of the input entities;
   providing each of the feature maps to each of a set of classifiers, and obtaining from each of the set of classifiers an assigned label for each of the plurality of feature maps, each of the set of classifiers being associated with one of the categories;
   comparing, for each of the set of classifiers, the assigned label for each of the plurality of feature maps to the target labels, to determine a plurality of gradients;
   masking the plurality of gradients according to each category, yielding a masked set of gradients for each of the categories; and
   training each of the set of classifiers according its associated masked gradients.

2. The method of claim 1, further comprising:
   providing an input entity to the first classifier, and obtaining therefrom a category of the input entity;
   determining a feature map for the input entity;
   providing the feature map to each of a set of classifiers, and obtaining from each of the set of classifiers a label for the feature map;
   masking the labels according to the category; and
   outputting the masked labels.

3. The method of claim 1, wherein each of the plurality of input entities comprises an image.

4. The method of claim 1, wherein the first classifier is pre-trained.

5. The method of claim 1, wherein the first classifier comprises an artificial neural network.

6. The method of claim 1, wherein each of the set of classifiers comprises an artificial neural network.

7. The method of claim 1, wherein each of the target labels is a member of one of the categories.

8. A computer program product for operating a plurality of classifiers, the computer program product comprising a computer readable storage medium having program instructions embodied therewith, the program instructions executable by a processor to cause the processor to perform a method comprising:
   reading a plurality of input entities, each of the input entities having an associated target label;
   providing the input entities to a first classifier, and obtaining therefrom a category of each of the input entities;
   determining a feature map for each of the input entities;
   providing each of the feature maps to each of a set of classifiers, and obtaining from each of the set of classifiers an assigned label for each of the plurality of feature maps, each of the set of classifiers being associated with one of the categories;
   comparing, for each of the set of classifiers, the assigned label for each of the plurality of feature maps to the target labels, to determine a plurality of gradients;
   masking the plurality of gradients according to each category, yielding a masked set of gradients for each of the categories; and
   training each of the set of classifiers according its associated masked gradients.

9. The computer program product of claim 8, the method further comprising:

provide an input entity to the first classifier, and obtaining therefrom a category of the input entity;

determining a feature map for the input entity;

providing the feature map to each of a set of classifiers, and obtaining from each of the set of classifiers a label for the feature map;

masking the labels according to the category; and outputting the marks labels.

10. The computer program product of claim 8, wherein each of the plurality of input entities comprises an image.

11. The computer program product of claim 8, wherein the first classifier is pre-trained.

12. The computer program product of claim 8, wherein the first classifier comprises an artificial neural network.

13. The computer program product of claim 8, wherein each of the set of classifiers comprises an artificial neural network.

14. The computer program product of claim 8, wherein each of the target labels is a member of one of the categories.

15. A method comprising:

inputting data into both: i) a plurality of fine-grained classifiers and ii) a course-grained classifier, the coarse grained classifier configured to categorize the input data among a plurality of masking modules, each of the plurality of masking modules corresponding to one of the plurality of fine-grained classifiers;

during a training phase, computing a loss function corresponding to each pair of the fine-grained classifiers and masking modules; and during an inference phase, assigning the data to a particular class in view of output from the plurality of fine-grained classifiers and the plurality of masking modules.

16. The method of claim 15, wherein the data comprise a plurality of images.

17. The method of claim 15, wherein the coarse classifier is pre-trained.

18. The method of claim 15, wherein the coarse classifier comprises an artificial neural network.

19. The method of claim 15, wherein each of the plurality of fine-grained classifiers comprises an artificial neural network.

* * * * *